United States Patent
Nelson et al.

(10) Patent No.: US 9,044,344 B2
(45) Date of Patent: Jun. 2, 2015

(54) GLENOID BASEPLATE INSERTION TOOL

(75) Inventors: Andrew Nelson, Upper Saddle River, NJ (US); Michael A. McGovern, Wyckoff, NJ (US); Jonathan You, Far Hills, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 416 days.

(21) Appl. No.: 13/526,682

(22) Filed: Jun. 19, 2012

(65) Prior Publication Data

US 2013/0338675 A1 Dec. 19, 2013

(51) Int. Cl.
*A61F 2/46* (2006.01)
*A61B 17/17* (2006.01)
*A61B 17/80* (2006.01)
*A61B 17/88* (2006.01)
*A61B 17/86* (2006.01)
*A61F 2/30* (2006.01)

(52) U.S. Cl.
CPC ............ *A61F 2/4612* (2013.01); *A61B 17/1728* (2013.01); *A61B 17/8894* (2013.01); *A61B 17/8888* (2013.01); *A61F 2002/4622* (2013.01); *A61B 17/808* (2013.01); *A61B 17/86* (2013.01); *A61F 2002/30565* (2013.01); *A61F 2002/30774* (2013.01); *A61F 2002/4627* (2013.01); *A61F 2002/4628* (2013.01)

(58) Field of Classification Search
CPC A61F 2/4603; A61B 17/1728; A61B 17/808; A61B 17/8888; A61B 17/8894
USPC ...................... 606/91, 96, 99, 100, 104, 86 B; 81/444–449, 451–456, 459
See application file for complete search history.

(56) References Cited

U.S. PATENT DOCUMENTS

| | | |
|---|---|---|
| 4,364,381 A | 12/1982 | Sher et al. |
| 7,367,979 B2 | 5/2008 | Abdelgany |
| 7,513,912 B2 | 4/2009 | Hayes, Jr. et al. |
| 7,651,502 B2 | 1/2010 | Jackson |
| 2004/0002758 A1 | 1/2004 | Landry et al. |
| 2005/0137606 A1* | 6/2005 | Binder et al. ................... 606/96 |
| 2010/0057138 A1* | 3/2010 | Murner et al. ................ 606/308 |

* cited by examiner

*Primary Examiner* — Michael T Schaper
(74) *Attorney, Agent, or Firm* — Lerner, David, Littenberg, Krumholz & Mentlik, LLP

(57) ABSTRACT

An insertion instrument for inserting an orthopedic implant into a bone and guiding an implant attachment element into the bone comprising: a body having a first end and a second end and a bore extending along a central axis; a fixed arm and a deflectable arm coupled to the body second end, the fixed arm spaced from the deflectable arm forming an attachment element receiving passageway therebetween extending along the central axis, the fixed arm having an implant engaging free end spaced a fixed distance from the central axis; and an actuator mounted on the first end of the body for moving the deflectable arm away from the fixed arm while allowing the attachment element to traverse the passageway.

22 Claims, 9 Drawing Sheets

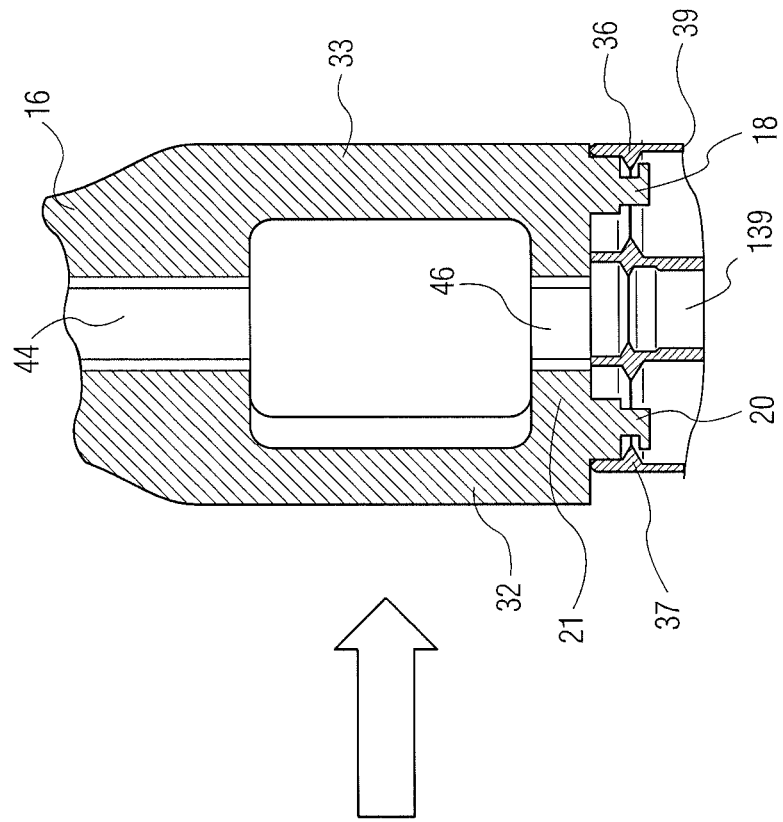
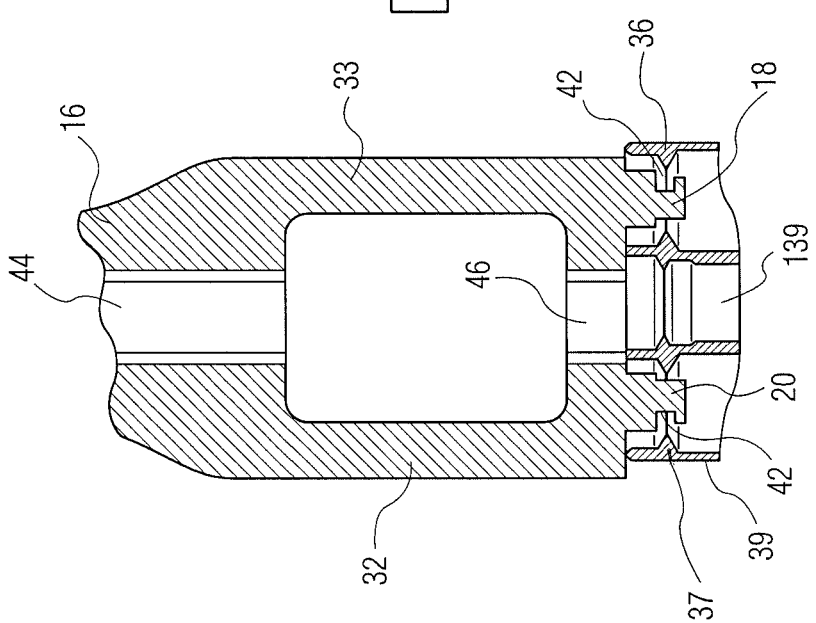

GLENOID BASEPLATE INSERTION TOOL

BACKGROUND OF THE INVENTION

In the field of total joint replacements it is often necessary to mount plates or bearing elements mounted on plates on resected or prepared joint surfaces for receiving or contacting other elements of the joint replacement. Although these plate-like implants may include tissue ingrowth surfaces, some form of initial attachment to bone is required. This initial attachment is often achieved by utilizing threaded elements such as bone screws to attach the plates to bone. For example tibial or glenoid implants may have plate like structures attached using screws.

It is sometimes necessary to hold an implant with one instrument and then insert the bone screw through the plate with a second instrument. In addition, when using bone screws it is sometimes desired to drill a pilot hole in the bone prior to inserting the screws so that insertion forces within the bone by the bone screw are lessened. Obviously once the plate has been implanted it is necessary to remove any instrumentation from the plate.

There has been a need for instrumentation which firmly grips an implant plate so that it may be located and held in position on the bone and can be used to simultaneously guide the insertion of a bone screw through a bore in the plate and into bone. This is particularly advantageous in shoulder operations where access to the glenoid area of the shoulder is somewhat limited.

BRIEF SUMMARY OF THE INVENTION

Therefore it is one aspect of this invention to provide an implant insertion system which provides positive attachment to a plate-like implant while permitting the insertion of a second implant, such as bone screw, through the instrument and a bore in the bone plate for attaching it to bone.

It is a further aspect of the invention to provide such an instrument for use in a glenoid application particularly for use in a reverse shoulder where a convex bearing element is coupled to the bone of the glenoid. An insertion instrument for inserting an orthopedic implant onto a bone and guiding an implant attachment element into the bone useful for plate implantation has a body having a first end and a second end and a bore extending along a central axis. The body has fixed arms and a deflectable arm coupled to the body second end. The fixed arm is spaced is from the deflectable arm forming an attachment element passageway, for example a bone screw receiving passageway therebetween extending along the central axis. The fixed arm has an implant engaging free end spaced a fixed distance from the central axis. An actuator is mounted on the first end of the body for moving the deflectable arm away from the fixed arm while allowing the attachment element or bone screw to traverse the passageway.

The bore in the body is at least partially threaded and the actuator has an outer threaded portion mating with the threaded bore in the body. The actuator includes a shaft having an internal bore co-axial with the central axis of the bore in the body. The bore allows the bone screw to pass through the actuator while the instrument is locked on the plate. The actuator shaft has a drive portion and/or handle portion extending outwardly of the first end of the body. The drive portion may be a lobed handle fixed to the shaft for rotation therewith which may be driven by hand. The fixed arm and the deflectable arm are integral with the body second end wherein the first end of the instrument body is a handle portion. The fixed arm may have a first width and the deflectable arm has a second width less than the first width. The fixed arm may have a width generally equal to a thickness of the handle. The deflectable arm is preferably positioned intermediate a pair of non-deflectable arms which are spaced a fixed distance from the fixed arm. Each of the pair of non-deflectable arms surrounding the deflectable arm have ends coupled to an end of the fixed arm.

The invention can also be achieved by a system for implanting an orthopedic implant having a plate for attachment to a bone comprising a through bore and first and second coupling elements on a non-bone contacting surface of the plate. An attachment element, for example a bone screw, can be inserted into the plate bore using an insertion instrument comprising a body having a first and second end and a bore extending along a central axis. A fixed arm and a deflectable arm coupled to the body second end. The fixed arm is spaced from the deflectable arm forming an attachment element or bone screw receiving passageway therebetween extending along the central axis. The fixed arm has an end spaced a fixed distance from the central axis, and a coupling element for engaging the plate first coupling element. The deflectable arm has an end with a coupling element for engaging the plate second coupling element. An actuator is mounted on the body first end for moving the deflectable arm away from the fixed arm. The actuator has an internal bore allowing the attachment element or bone screw to traverse the passageway between the fixed and deflectable arms into the plate through bore.

The bore in the body is at least partially threaded. The actuator has a shaft with an outer threaded portion mating with the threaded bore in the body and the actuator shaft internal bore is co-axial with the central axis of the bore in the body when mounted thereon. The actuator shaft has a rotatable drive portion extending outwardly of the first end of the instrument body. The drive portion is a handle, preferably a handle having multiple lobes for easy gripping with one's hand. The fixed arm and the deflectable arm are integral with the body second end. The first end of the instrument may be in form of a handle. The fixed arm has a first width and the second arm has a second width less than the first width. The deflectable arm is housed intermediate a pair of non-deflectable arms spaced from the fixed arm in a direction perpendicular to the axis by a crossmember at the end of the instrument. The crossmember is connected to the fixed arm and each non-deflectable arm and defines an opening for the bone screw intermediate the arms. Each of the pair of non-deflectable arms have ends fixed by the connector to an end of the fixed arm.

BRIEF DESCRIPTION OF THE DRAWINGS

FIG. 2A is a view looking towards the middle of the instrument along lines 2A-2A of FIG. 2 with the gripping arms in a relaxed non-engaged position;

FIG. 2B shows the view of FIG. 2A with the arms expanded against the base plate in an engaged position;

DETAILED DESCRIPTION

Figure 4:
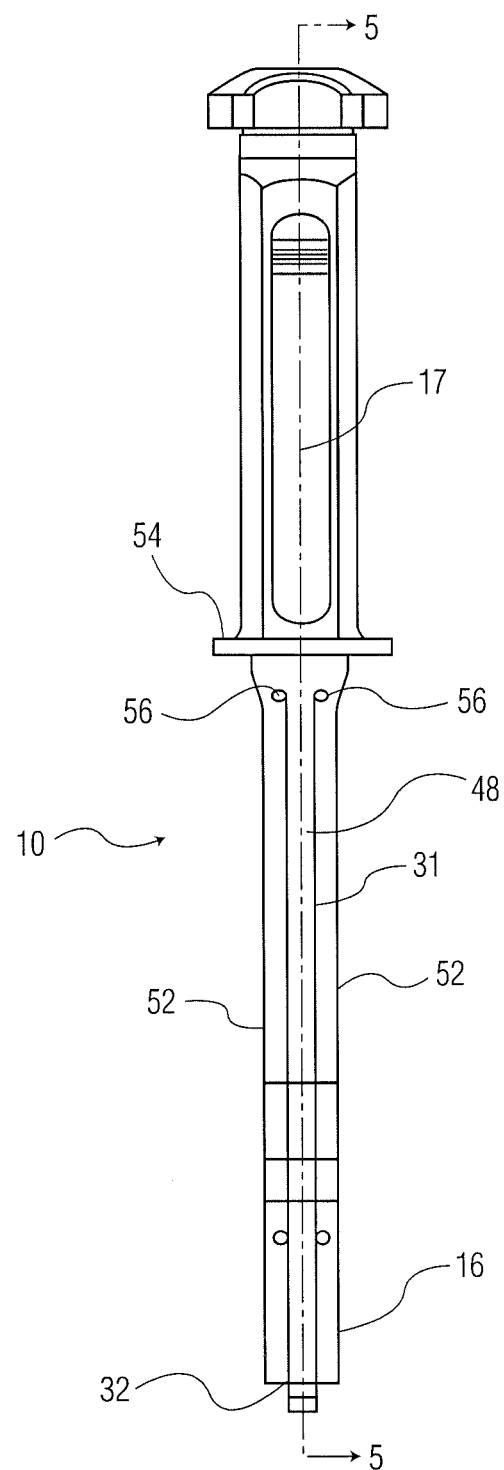
FIG. 4 is a side view of the base plate insertion tool of FIG. 3.
Figure 5:
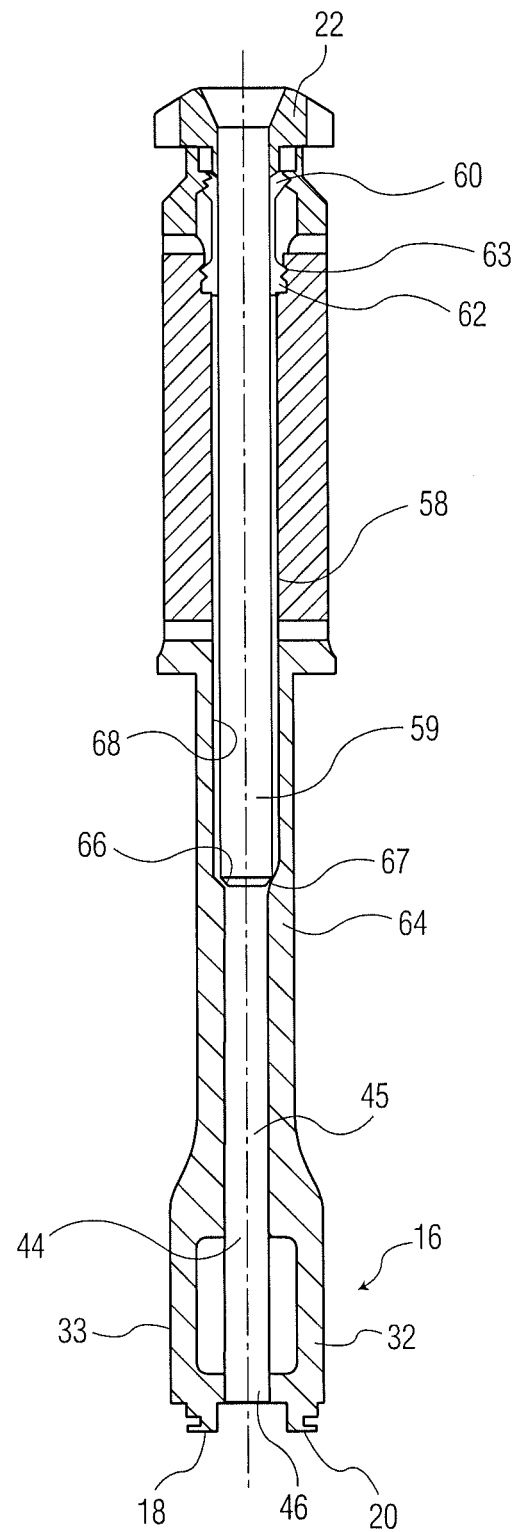
FIG. 5 is a cross-sectional view of the base plate insertion tool of FIG. 4 along lines 5-5
Figure 6:
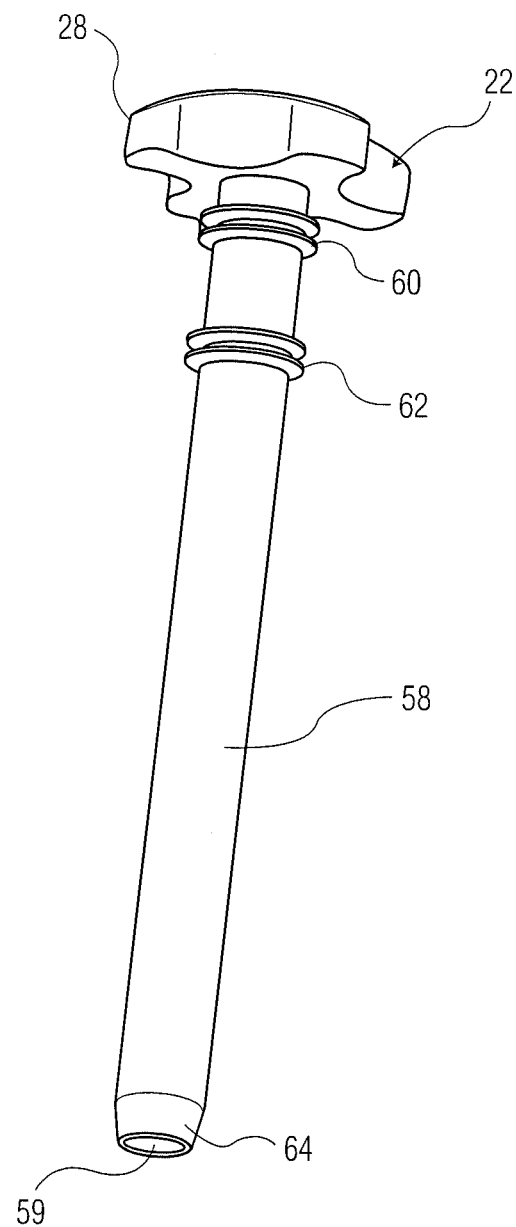
FIG. 6 is an isometric view of the axially movable actuator shown in the previous figures.

Referring to FIGS. 1 to 6 there is shown an isometric view of an insertion tool of the present invention generally denoted as 10. Tool 10 has a first end including an axially movable actuator 22 including an opening 30, a handle portion 12 fixedly coupled to a shaft portion 14 including a second or leading end 16 which includes a pair of coupling elements 18 and 20. Coupling element 18 is mounted on a fixed crossmember 19. Element 20 is mounted on a resiliently deflectable arm member 21 received within crossmember 19 and element 18 is located on non-deflectable (fixed) arm 38 which is part of crossmember 19. Arm member 21 is coupled to leg 32 and member 38 is coupled to leg 33. Handle portion 12, shaft portion 14 and leading end 16 extend along a central longitudinal axis 17. The insertion tool 10 is cannulated along axis 17 and has an axially moveable actuator 22 extending within an opening through handle portion 12 and through a bore in shaft 14. Actuator 22 shown in FIG. 6 is also cannulated by a bore 30a so that the entire assembly can receive a bone screw or other bone attachment implant through opening 30 which leads to bore 59 and implant a base plate onto bone. The axis of the bore 59 in actuator 22 is coaxial with axis 12 of insertion tool 10.

Figure 1:
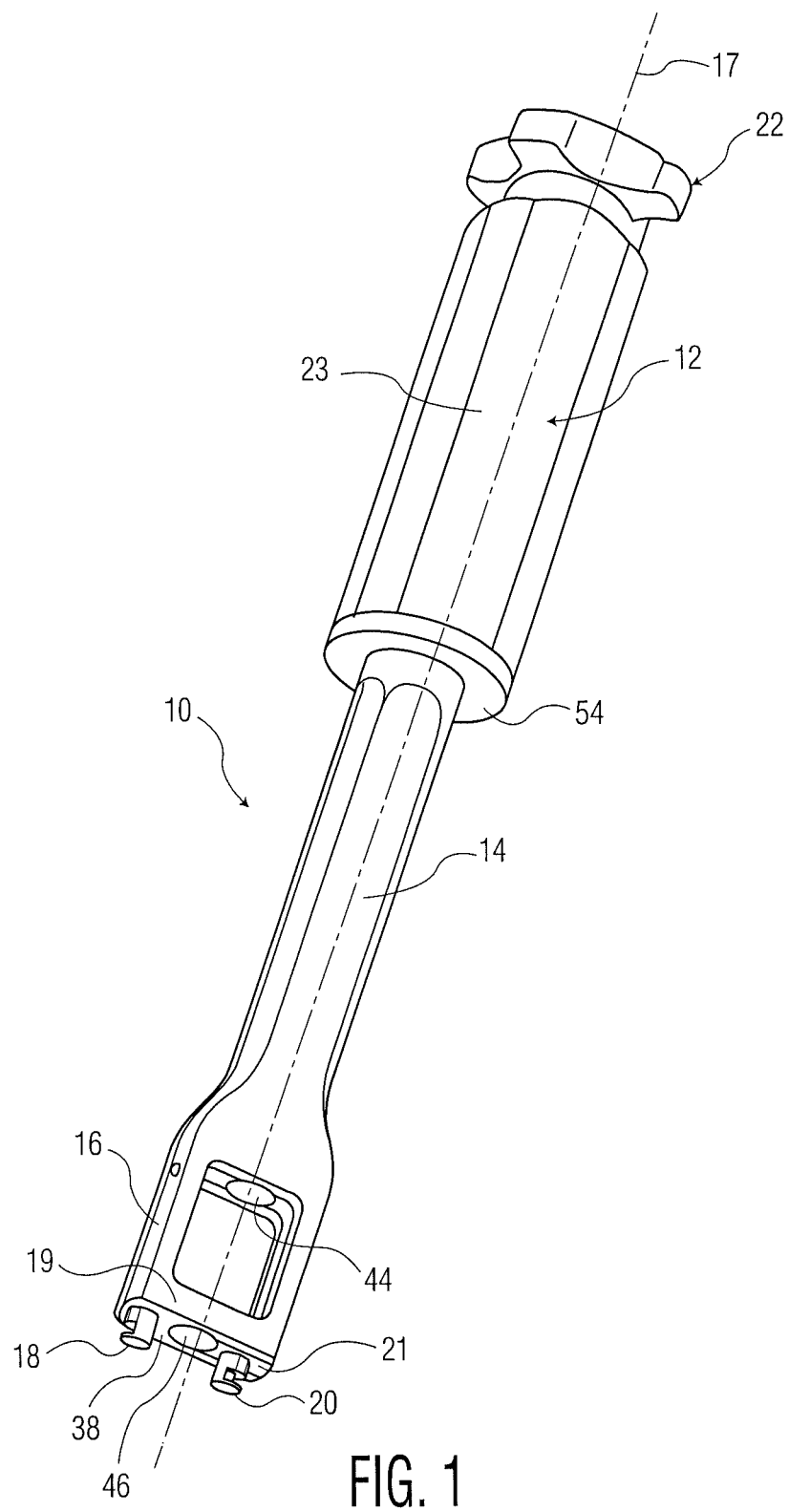
FIG. 1 is an isometric view of a base plate insertion tool viewed from the front.
Figure 1A:
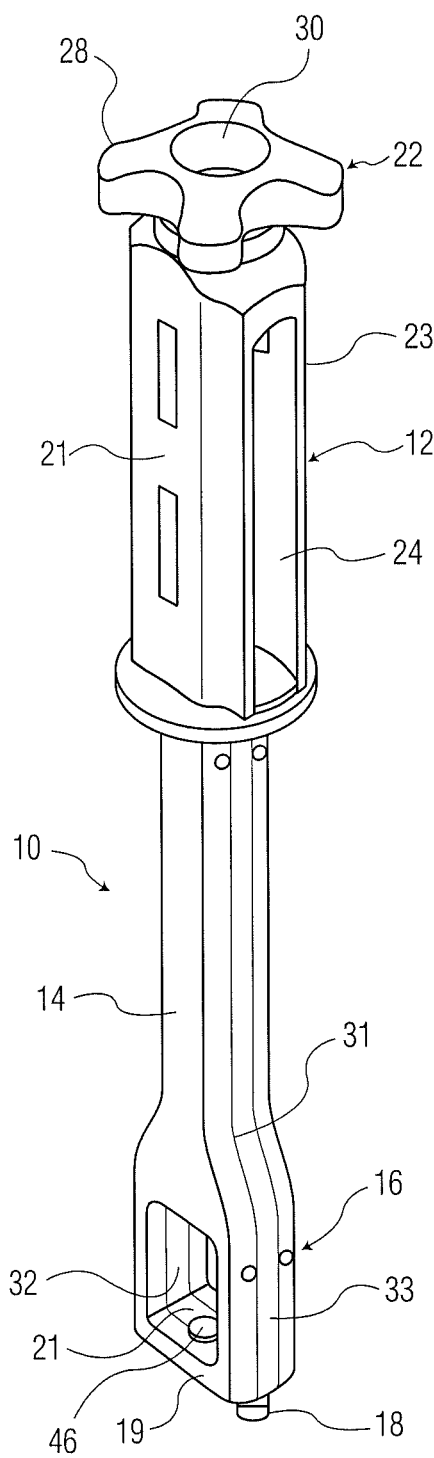
FIG. 1A is an isometric view of the base plate insertion tool of FIG. 1 when viewed from the side.
Figure 2:
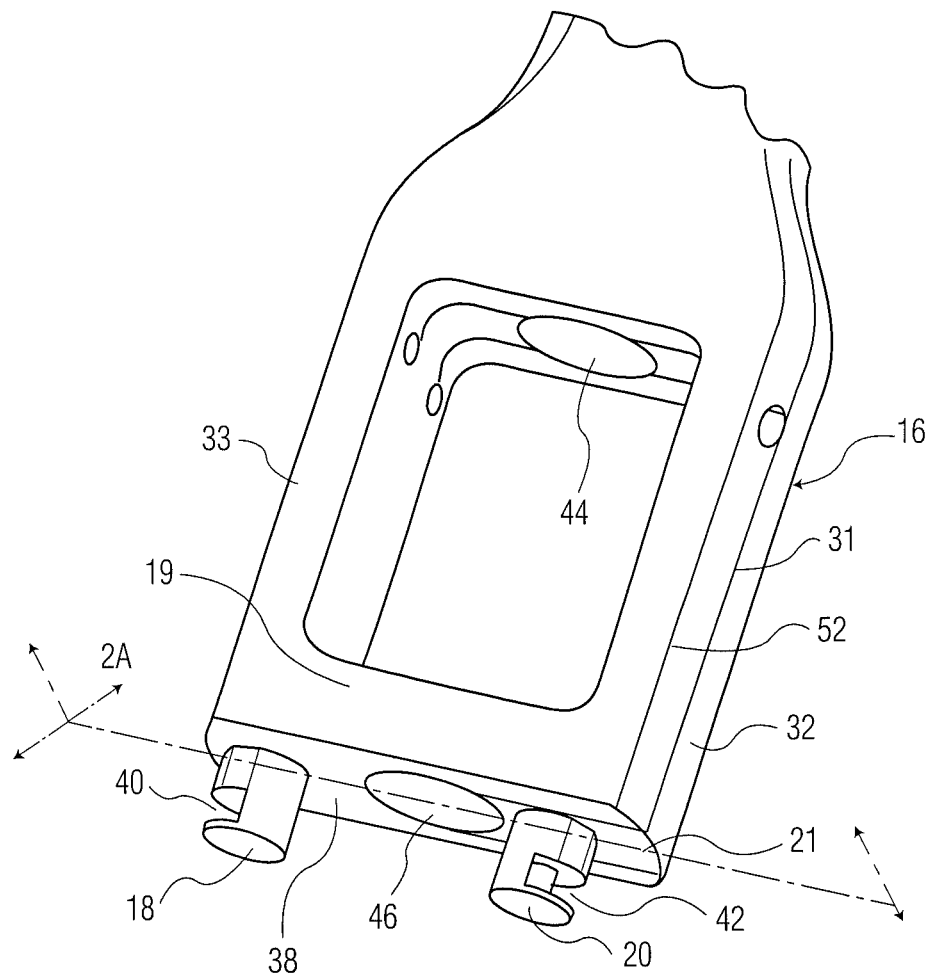
FIG. 2 is an enlarged view of the leading end of the insertion tool of FIGS. 1 and 2 having coupling elements adapted to engage an implant base plate.

Referring to FIGS. 1A and 6 it can be seen that handle 12 is comprised of two side plates 21 and 23 spaced to form a recess 24 allowing viewing of the outer surface of a shaft 58a of actuator 22. Actuator 22 includes a handle 28 so that it may be rotated and axially moved as will be discussed below. Bore 59 of actuator 22 also allows for the insertion of a screwdriver through tool 10 to drive a bone screw into bone. End 16 of tool 10 also includes a pair of openings 44 and 46 to allow passage of the bone screw and screw driver. Opening 44 is at the end of shaft portion 14 and opening 46 is in crossmember 19. Shown as fine lines in both FIGS. 1 and 1A, are slits 31 which extend through the leading end 16 of the insertion tool which allows arm member 21 and leg portion 32 of the leading end to deflect outwardly with respect to shaft portion 14 and handle 12. Crossmember 19 and the other leg 33 is fixed with respect to handle 12. As will be discussed below, these slits may be created by electrical discharge machining (EDM).

Figure 7:
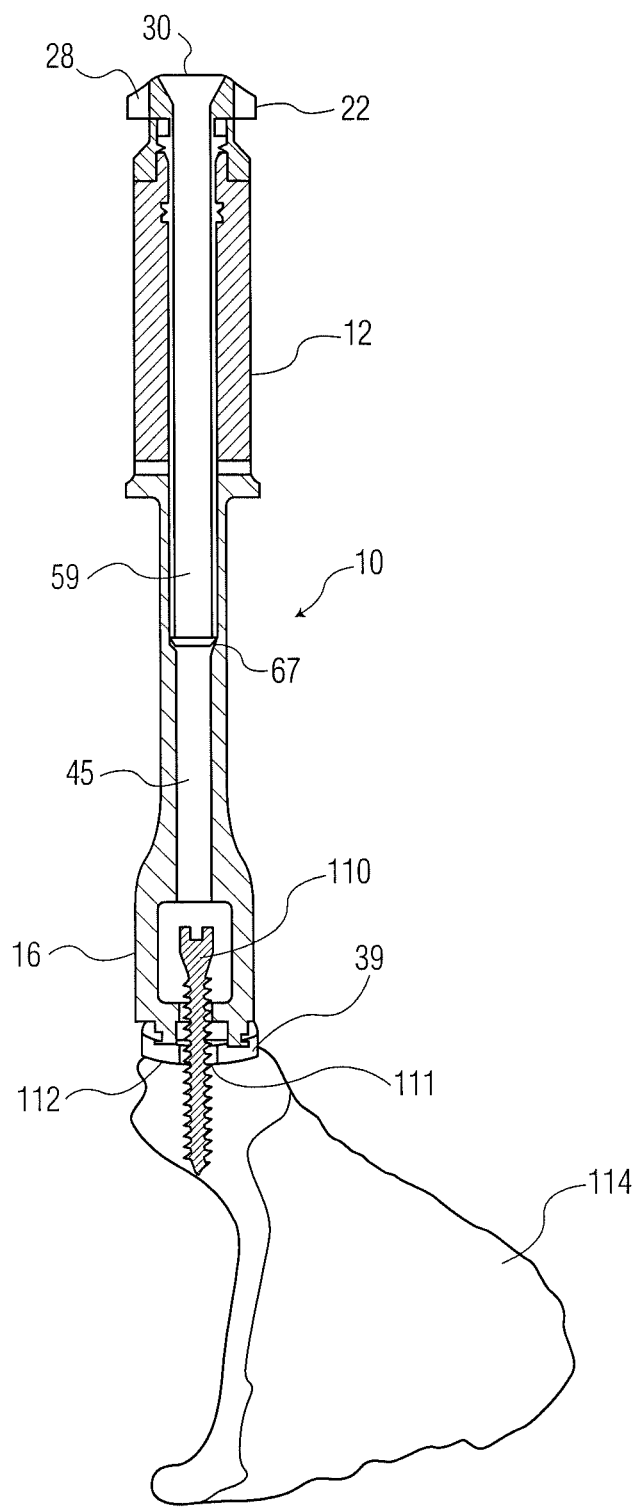
FIG. 7 shows the base plate insertion tool of the present invention connected to a base plate after a second implant, such as a bone screw, has been located and inserted through the base plate.

Referring to FIGS. 2, 2A, 2B and 3 there is shown an enlarged view of the leading end 16 of the insertion instrument 10 which includes fixed coupling element 18 mounted on an end surface of a fixed arm 38 and element 20 mounted on an end surface of deflectable arm 21. Elements 18 and 20 are peg-like extensions having recesses 40 and 42 respectively. Recesses 40 and 42 are adapted to receive mating coupling elements 36 and 37 on a base plate 39. As shown in FIG. 7 a bore 139 is provided in baseplate 39 for a bone screw.

Leading end 16 of instrument 10 includes bores 44 and 46 through which a bone implant such as a bone screw can traverse. End 16 includes deflectable leg 32 and deflectable arm 21 and fixed leg 33 and fixed arm 38. Coupling element 20 is integral with arm 21 and moves with the deflection of legs 32 and arm 21. Leg 32 is separated from a pair of non-movable legs 52 by slits 31. Non-deflectable legs 52 are on either side of deflectable leg 32 and are each connected to fixed leg 33 by crossmember 19. Crossmember 19 includes bore 46 which may intersect slits 31 to allow leg 32 and arm 21 to deflect. Preferably deflectable leg 32 formed by slits 31 extends from adjacent a plate 54 at the base of handle portion 12 all the way to end surface of arm 21. Referring to FIGS. 2A and 2B, there is shown enlarged leading ends 16 of shaft portion 14 coupled to a base plate 39. Base plate 39 may be attached to a glenoid and includes a central bore 139 for receiving a bone screw. In FIG. 2A the legs 32 and 33 are in a relaxed position whereas in FIG. 2B they are in an expanded engaged position. As can be seen in the expanded position, leg 32 and arm 21 shift outwardly thereby expanding holes 44 and 46 about 0.3 inches so that recess 42 of legs 18 and 20 engage coupling elements 36 and 37 on base plate 39. As will be discussed below, rotation of handle 22 forces deflectable leg 32 and arm outwardly thereby moving coupling element 20 into tight engagement with the coupling element 37 on base plate 39. Slits 31 extend inwardly between legs 52 and leg 32 to the cannulated central bore of the instrument 10 from adjacent plate 54 so that the actuator 22 can cause the deflection of leg 32. Slits 31 end in small through bores 56 which provide additional flexibility and which make using EDM easier by providing a starting location.

Figure 3:
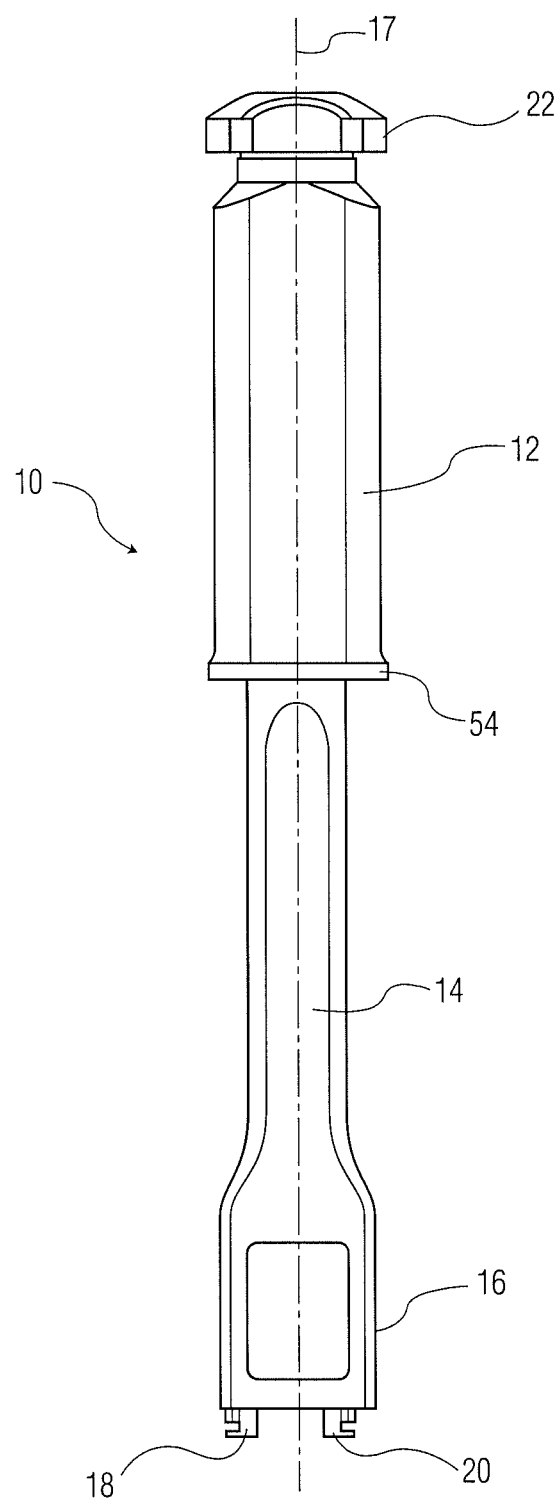
FIG. 3 is a front view of the base plate insertion tool of FIGS. 1 and 1A.

Referring to FIGS. 3-5 there is shown various views of the insertion instrument of the present invention. As can be seen in FIG. 4, slits 31 extend from bores 56 adjacent plate 54 to the end surface of arm 21 of leading end 16 of instrument 10. Referring to FIGS. 5 and 6, there is shown actuator 22 which includes a cylindrical cannulated shaft or tube portion 58 inserted in and surrounding bore 59. The outer surface of shaft 58 includes threaded portions 60 and 62 which threadably engage helical threaded portions 63. Shaft portion 14 of insertion tool 10 includes a bore 45 ending in opening 44. Shaft 58 has a tapered free end 64 best shown in FIG. 6. End 64 is preferably a section of a cone tapering inwardly towards axis 17. The diameter of bores 45 and 59 are sufficiently large to accommodate the head of the bone screw or other attachment element which attaches the base plate to the glenoid.

During manufacturing, the bore 59 is machined with the leg 33 deflected outwardly 0.3 inches so that a ramp 67 is formed when the deflected leg 33 springs inwardly. The ramp 67 is about halfway down the bore 59. As a result of this manufacturing method the leg will deflect 0.3 inches at the distal end when the center tube is fully inserted and there is no baseplate attached to the instrument. When the baseplate 39 is attached to the instrument 10 the spring deflection is only allowed to be about 0.125 inches before the baseplate is fully engaged by the instrument. To fully engage the baseplate requires about 1 full turn of the center tub 58 based on the pitch and location of the thread at the top of the center tube.

The slits 31 are about 0.010 inches wide, which width is obtained using the thinnest wire available for the wire EDM. Having thinner slits means that there is less rotational "slop" in the design. The spring arm is about 4.75 inches long, and the part is about 0.050 inches thick where the spring arm attaches to the rest of the instrument. The spring arm thickness is not a constant 0.050 inches, and for example is about 0.080 inches thick just below a ramp 67 formed on an inner surface of the spring arm 33. These dimensions are for stainless steel, and using other metals may require modifications to either the spring element dimensions, the force required to screw in the center tube, and/or the thread pitch at the top of the center tube.

As can be seen in FIG. 5 as handle 22 is rotated clockwise screw portions 60 and 62 engage threads 63 and cause the tapered outer surface 66 of end 64 to advance and engage ramp 67 formed on the inner facing surface of arm 33 in the area at the end of an enlarged bore portion 68 of cannulated bore 45. As shaft 58 advances axially upon rotation toward end 16 arm 32 coupling element 20 is deflected outwardly of axis 17. Portion 68 is sized to accommodate an outer diameter of tubular shaft 58 while still allowing bore 59 to be large enough to allow the screw head to pass through bore 59 and bore 45 of the instrument 10.

Referring to FIG. 7 there is shown instrument 10 coupled to base plate 39 with a bone screw 110 partially inserted through a bore 111 in base plate 39. Actuator 22 has been axially advanced towards end 16 of instrument causing leg 32 and arm 21 to deflect outwardly and lock the instrument to the baseplate 39 by the engagement of pins 18 and 20 and elements 36 and 39. Screw 110 has been previously passed through cannulated bores 45 and 59 along with a drive tool (not shown), such as a screwdriver, and driven into the glenoid area 112 of scapula 114. When screw 110 is fully seated on base plate 39 by use of the screwdriver (not shown) handle 22 is rotated counterclockwise thus allowing arm 21 and leg 32 to spring back into its original position in alignment with arms 52 so that coupling element 20 is disengaged from the coupling element 37 on the base plate 39. At this point there is sufficient clearance between the coupling elements 18 and 20 on the insertion tool and the coupling elements 36, 37 on base plate 39 to allow removal of the tool from the glenoid site.

While the insertion tool has been described for use in connection with a glenoid base plate, it could also be used for example with a tibial base plate or any implant requiring a bone screw to be inserted while the implant, such as a bone plate, is held in position on the bone by tool 10.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An insertion instrument for inserting an orthopedic implant into a bone and guiding an implant attachment element into the bone comprising:
a body having a first end and a second end and a bore extending along a central axis, the body having a frontwardly and a rearwardly facing surface, the body second end having an open portion extending between the frontwardly facing surface and the rearwardly facing surface;
a fixed arm and a deflectable arm coupled to the body second end, the fixed arm at least partially spaced from the deflectable arm by the open portion, the bore in body forming an attachment element receiving passageway extending along the central axis of the body, the fixed arm and the deflectable arm each having an implant engaging element at a free end spaced from the central axis, the deflectable arm defined by a pair of slits located intermediate the body frontwardly and rearwardly facing surfaces and extending to the open portion; and
an actuator mounted on the first end of the body for moving the deflectable arm away from the bore central axis in a direction away from the open portion so that the deflectable arm implant engaging element moves away from the central axis while allowing the attachment element to traverse the passageway, the implant engaging element of the fixed arm remaining a constant distance from the central axis while the deflectable arm implant engaging element moves away from the central axis.

2. The instrument as set forth in claim 1 wherein the bore in the body is at least partially threaded.

3. The instrument as set forth in claim 2 wherein the actuator has a shaft with an outer threaded portion mating with the bore in the body and the shaft has an internal bore co-axial with the central axis of the bore in the body.

4. The instrument as set forth in clam 3 wherein the actuator shaft has a drive portion extending outwardly of the first end of the body.

5. The instrument as set forth in claim 4 wherein the drive portion is a handle fixed to the shaft for rotation therewith.

6. The instrument as set forth in claim 1 wherein the fixed arm and the deflectable arm are integral with the body second end.

7. The instrument as set forth in claim 1 wherein the first end of the instrument body is a handle portion.

8. The instrument as set forth in claim 1 wherein the fixed arm has a width defined by a distance between the forwardly and rearwardly facing surface.

9. The instrument as set forth in claim 8 wherein the deflectable arm is positioned intermediate a pair of non-deflectable arms defined by the distance between the pair of slits and the respective forwardly and rearwardly facing surfaces which non-deflectable arms are spaced a fixed distance from the fixed arm.

10. The instrument as set forth in claim 9 wherein each of the pair of non-deflectable arms has an end fixedly coupled to an end of the fixed arm.

11. The instrument as set forth in claim 1 wherein the attachment element is a bone screw.

12. A system for implanting an orthopedic implant plate comprising:
a plate for attachment to a bone comprising a through bore and first and second coupling elements on a non-bone contacting surface of the plate;
an attachment element for extending into the bone through the through bore of the plate;
an insertion instrument comprising a body having a first and second end and a bore extending along a central axis, a fixed arm and a deflectable arm coupled to the body second end, the fixed arm spaced from the deflectable arm forming a passageway for the attachment element extending along the central axis, the fixed arm having an end spaced a fixed distance from the central axis, and a first coupling element for engaging the plate first coupling element, the deflectable arm having an end with a second coupling element for engaging the plate second coupling element and an actuator mounted on the body first end for moving the deflectable arm away from the central axis, the actuator having a bore allowing the attachment element to traverse the passageway into the plate through bore, the body having oppositely facing first and second outer surfaces with the fixed arm extending between the first and second surfaces, the deflectable arm having side surfaces spaced intermediate the first and second outer surfaces, the actuator moving the second coupling element away from the central axis while the first coupling element on the fixed arm remains at a constant distance from the central axis.

13. The system as set forth in claim 12 wherein the bore in the body is at least partially threaded.

14. The system as set forth in claim 13 wherein the actuator has a shaft with an outer threaded portion mating with the bore in the body and the shaft having an internal bore co-axial with the central axis of the bore in the body.

15. The system as set forth in clam 14 wherein the actuator shaft has a drive portion extending outwardly of the first end of the instrument body.

16. The system as set forth in claim 15 wherein the drive portion is a handle.

17. The system as set forth in claim 12 wherein the fixed arm and the deflectable arm are integral with the body second end.

18. The system as set forth in claim 12 wherein the first end of the instrument is a handle.

19. The system as set forth in claim 12 wherein the fixed arm has a first width and the second arm has a second width less than the first width.

20. The system as set forth in claim 19 wherein the deflectable arm is housed intermediate a pair of non-deflectable arms spaced from the fixed arm.

21. The system as set forth in claim 20 wherein each of the pair of non-deflectable arms has an end fixed to an end of the fixed arm.

22. The system as set forth in claim 12 wherein the attachment element is a bone screw.

\* \* \* \* \*